United States Patent
Kepler et al.

(10) Patent No.: US 7,633,267 B2
(45) Date of Patent: Dec. 15, 2009

(54) APPARATUS FOR COMBINATORIAL SCREENING OF ELECTROCHEMICAL MATERIALS

(75) Inventors: Keith Douglas Kepler, Belmont, CA (US); Yu Wang, Foster City, CA (US)

(73) Assignee: Farasis Energy, Inc., Hayward, CA (US)

( * ) Notice: Subject to any disclaimer, the term of this patent is extended or adjusted under 35 U.S.C. 154(b) by 386 days.

(21) Appl. No.: 11/175,555

(22) Filed: Jul. 5, 2005

(65) Prior Publication Data

US 2006/0001430 A1 Jan. 5, 2006

Related U.S. Application Data

(60) Provisional application No. 60/584,969, filed on Jul. 2, 2004.

(51) Int. Cl.
*H01M 10/46* (2006.01)
(52) U.S. Cl. ..................................................... 320/150
(58) Field of Classification Search ................ 320/101, 320/107, 112, 116, 150; 429/30, 40, 44
See application file for complete search history.

(56) References Cited

U.S. PATENT DOCUMENTS

| | | | |
|---|---|---|---|
| 6,187,164 B1 | 2/2001 | Warren | |
| 6,410,331 B1 | 6/2002 | Schultz | |
| 6,536,944 B1 * | 3/2003 | Archibald et al. | 506/12 |
| 6,683,446 B1 * | 1/2004 | Pope et al. | 324/71.1 |
| 6,686,205 B1 | 2/2004 | Schultz | |
| 6,690,179 B2 * | 2/2004 | Hajduk et al. | 324/452 |
| 2002/0009627 A1 | 1/2002 | Smotkin | |
| 2002/0028456 A1 | 3/2002 | Mansky | |
| 2003/0070917 A1 | 4/2003 | Giaquinta | |
| 2003/0138025 A1 | 7/2003 | Archibald | |
| 2004/0224204 A1 | 11/2004 | Smotkin | |

FOREIGN PATENT DOCUMENTS

| | | |
|---|---|---|
| WO | WO 99/34206 | 7/1999 |
| WO | WO 00/04362 | 1/2000 |
| WO | WO 02/05367 | 1/2002 |

OTHER PUBLICATIONS

Reddington, E.; Combinatorial electrochemistry: . . . , Science, vol. 280 Jun. 12, 1988, p. 1735.
Rongzhong, J.; A combinatorial approach toward electrochemical analysis, Journal of Electroanalytical Chemistry, vol. 527, 2002, p. 137.
Sullivan, M; Automated electrochemical analysis . . . , Analytical Chemistry, vol. 71, 1999, p. 4369.

* cited by examiner

*Primary Examiner*—Edward Tso
(74) *Attorney, Agent, or Firm*—Schein & Cai LLP; James (Jingming) Cai

(57) ABSTRACT

A high throughput combinatorial screening method and apparatus for the evaluation of electrochemical materials using a single voltage source (2) is disclosed wherein temperature changes arising from the application of an electrical load to a cell array (1) are used to evaluate the relative electrochemical efficiency of the materials comprising the array. The apparatus may include an array of electrochemical cells (1) that are connected to each other in parallel or in series, an electronic load (2) for applying a voltage or current to the electrochemical cells (1), and a device (3), external to the cells, for monitoring the relative temperature of each cell when the load is applied.

20 Claims, 4 Drawing Sheets

APPARATUS FOR COMBINATORIAL SCREENING OF ELECTROCHEMICAL MATERIALS

RELATED APPLICATIONS

This patent claims the benefit of Provisional Patent Application Ser. No. 60/584,969, filed Jul. 2, 2004, the disclosure of which is herein incorporated by reference in its entirety.

FEDERALLY SPONSORED RESEARCH

The invention was made under support of the United States Government, Department of Energy, Small Business Innovative Research Grant Number DE-FG02-03ER83656. The United States has certain rights in the invention.

SEQUENCE LISTING OR PROGRAM

Not applicable

FIELD OF THE INVENTION

The present invention relates to a high throughput combinatorial screening method and apparatus for the evaluation of electrochemical materials using a single voltage source. More particularly, this invention relates to a highly parallel apparatus and method for screening electrochemical materials based on their relative electrochemical efficiency by simultaneously monitoring the temperature change of electrodes within multiple electrode arrays arising from power losses during the application of an electrical load.

BACKGROUND OF THE INVENTION

Electrochemical reactions form the basis of many important commercial applications. For example, batteries and fuel cells utilize electrochemical reactions to convert the dormant energy stored in chemical reactants into electricity. Additionally, several large-scale synthetic processes involve electrochemical reactions including the electrolysis of salts or solutions to produce elemental forms of active materials such as aluminum, lithium and sodium. In each of these types of applications, the performance and thus the value of the device or process is limited by the materials used. In particular, it is highly desirable that the application or process be highly efficient, thus maximizing energy conversion in the case of batteries and fuel cells and minimizing energy costs in the case of electrolytic processes.

Applications and processes that have poor electrochemical efficiency suffer losses of much of the available or supplied energy in the form of heat generation according to the equation $\Delta H = P \Delta t = i^2 R \Delta t$, where R is the effective resistance of the cell, i is the current density, P is the power loss and $\Delta t$ is time. Thus more energy is lost to heat generation when operating an inefficient electrochemical process relative to a more efficient process. In the case of a battery or fuel cell, a more efficient device will exhibit greater power density and greater energy density, particularly when the power demand is high. In fact, much of the design and cost of a battery or fuel cell system, particularly for large, high-power systems used in applications such as electric and hybrid electric or fuel cell vehicles, involves the minimization and management of heat generated by the system during operation.

The efficiency of an electrochemical process or device is dependent on many factors. These factors include the design of the electrochemical cell, the materials used to make the cell, the kinetics of the reactions occurring in the cell, and the multiple interactions of the various materials comprising the cell. To obtain a truly accurate measure of the performance potential of a specific electrochemical material composition, it is critical that all of these issues and interactions are part of the testing environment. For example in a Li-ion battery, the efficiency of the battery can be affected by a number of factors including the kinetics of the intercalation reaction at both the anode and cathode, the electrical conductivity of the anode and cathode, the porosity of the anode and cathode electrodes, the conductivity of the electrolyte, or the porosity of the separator among other factors. In a fuel cell, the efficiency of energy conversion can be greatly affected by the catalyst over-potential, which must be minimized, electrode composition and fuel distribution.

Thus, it is highly desirable to evaluate new electrochemical material candidates in a conventional cell that provides a testing environment similar to that for which the material is intended. This can be particularly important for systems in which interactions between the anode and cathode chemistry can affect the material performance. Such phenomena are common in both battery and fuel cell systems. For a battery or fuel cell a conventional cell commonly comprises a membrane tightly sandwiched between two electrodes; an anode at which oxidation occurs, and a cathode at which reduction occurs. An electrolyte for ion conduction is shared by the anode and cathode.

Because of the importance of the testing environment most electrochemical materials development is still done in series, where individual cells are made for each material and evaluated utilizing a single electronic load or cycler channel for each cell. Traditional current-voltage methods are employed to probe the performance of the materials over long periods of time, requiring large numbers of cycler channels, electronic loads and monitoring equipment. For example, one of the key performance criteria for hybrid electric vehicle batteries and fuel cells is that the there be little change in the resistance or efficiency of the device over the 10-15 year life of the application. Such long-term performance requirements make serial development of materials for such applications extremely difficult and costly since in many cases a single channel could potentially be occupied for months if not years simply to evaluate one material composition or cell design.

Predictive calculation and modeling of the performance of new electrochemical materials could mitigate some of the development burden. Unfortunately, many interfacial electrocatalytic reactions, such as those on which a hydrogen fuel cell is based, are very complex and not readily predisposed to rational catalyst design and many of the factors that affect the life of a battery or fuel cell are not well understood and thus difficult to accurately model. As a result, it can be a very time consuming process to discover and optimize new, more efficient electrochemical material compositions by conventional methods. A combinatorial approach to materials discovery, in which many compositions can be evaluated simultaneously and accurately, can be greatly beneficial to this process, and can be very valuable to the battery, fuel cell and electrolytic industries.

A number of methods have already been developed to screen various electrochemical materials combinatorially. Most of these methods involve the creation of arrays of electrodes or electrochemical cells on a single substrate, each individually addressable by an isolated electrical connection. Examples include U.S. Pat. No. 6,187,164 and US Published Patent Application Nos. 2002/028456 and 2003/0070917. While semiconductor processing methods have allowed large arrays to be made on very small substrates, testing of the materials still require a large number of electrochemical testing channels to probe each electrode by conventional voltage-current techniques. Furthermore, the electrode array structures generally do not allow for the design of electrochemical testing conditions that accurately simulate the environment in which the material will be utilized. For example, the members of the electrode array are commonly tested under half-cell conditions in a flooded cell environment. Semiconductor processing methods have also been used to make similar material arrays for testing a variety of non-electrochemical processes. For example, thermal imaging of sputter deposited alloys has been used as a probe of conventional catalytic reactions, as disclosed in published international application WO 99/34206, and of phase changes of materials, as disclosed in U.S. Pat. No. 6,536,944.

A conventional fuel cell device has been developed that can test multiple fuel cell catalysts in parallel against a common electrode to ensure more accurate comparison and evaluation of the catalyst samples. This device also uses conventional voltage and current techniques to probe performance and requires individual current monitoring channels for each electrochemical sample, as disclosed in US Published Patent Application Nos. 2002/0009627 and 2004/0224204. A highly parallel indirect screening method has been developed, also primarily for fuel cell catalysts. The method and devices using the method rely on indicator molecules to provide an optical signal whose intensity is related to the extent of the reaction of interest, as disclosed in published international applications WO 2000/04362 and WO 2002/05367. As an indirect method, a single voltage source can be used to power the device and simultaneously probe a large number of catalyst samples. However, a clear line of vision of the reaction front is required, preventing the use of conventional cell designs and diminishing the accuracy of the screening method. Furthermore, there are also many electrochemical processes for which suitable indicator molecules have not been identified.

Despite these advances, a combinatorial method for screening a large number of electrochemical materials samples over long periods of time and in conventional cell environments at a reasonable cost is needed.

SUMMARY OF THE INVENTION

The present invention provides an apparatus and method to combinatorially screen a plurality of electrochemical material compositions for use in an electrochemical cell such as a fuel cell, battery or electro-catalytic cell.

In one aspect of the invention an apparatus may comprise an array of electrochemical cells that are connected to each other in parallel or in series, an electronic load for applying a voltage or current to the electrochemical cells, and a device, external to the cells, for monitoring the relative temperature of each cell when the load is applied. The temperature of each cell under the load may be used as a relative measure of the electrochemical efficiency of the cells and of the material compositions contained therein. The electrochemical cells may share at least one membrane or separator. The electrochemical cells may share at least one common electrode. The electrochemical cells may further comprise discreet compositions of electrode materials. The electrochemical cells may be capable of being operated in a single fuel cell assembly. The electrochemical cells may further comprise a catalyst. The catalyst may be a fuel cell catalyst. The catalyst may be applied to a carbon diffusion layer or to a membrane. The device for monitoring the temperature of the cells may be a thermal imaging device, infrared camera or array of thermocouples.

In another aspect of the invention, a combinatorial method for screening and evaluating electrochemical material compositions may be based on an indirect thermal signature related to the efficiency of electrochemical cells comprising the material compositions. The method may begin with the provision of the electrochemical material composition. The material may then be incorporated into an electrochemical cell within an array of cells. The next step may include the electrical connection of the cells in parallel or in series. A potential or current may be applied to the electrochemical cell array and the temperature associated with the cell monitored. The relative efficiency of the electrochemical material composition may be determined from the temperature measurements. The electrochemical materials may include catalysts. The catalysts may be incorporated into the cell by deposition onto the sample electrodes. The deposition process may involve electrodeposition or may involve sputter deposition. The method may further include the compositional analysis of the materials before and after screening.

Additional advantages of the invention will become readily apparent to those skilled in the art from the following detailed description, wherein only the preferred embodiments of the invention are shown and described, simply by way of illustration of the best mode contemplated for carrying out the invention. As will be realized, the invention is capable of other and different embodiments, and its details are capable of modifications in various obvious respects, all without departing from the invention. Accordingly, the drawings and description are to be regarded as illustrative in nature and not as restrictive.

DETAILED DESCRIPTION OF THE INVENTION

Figure 1:
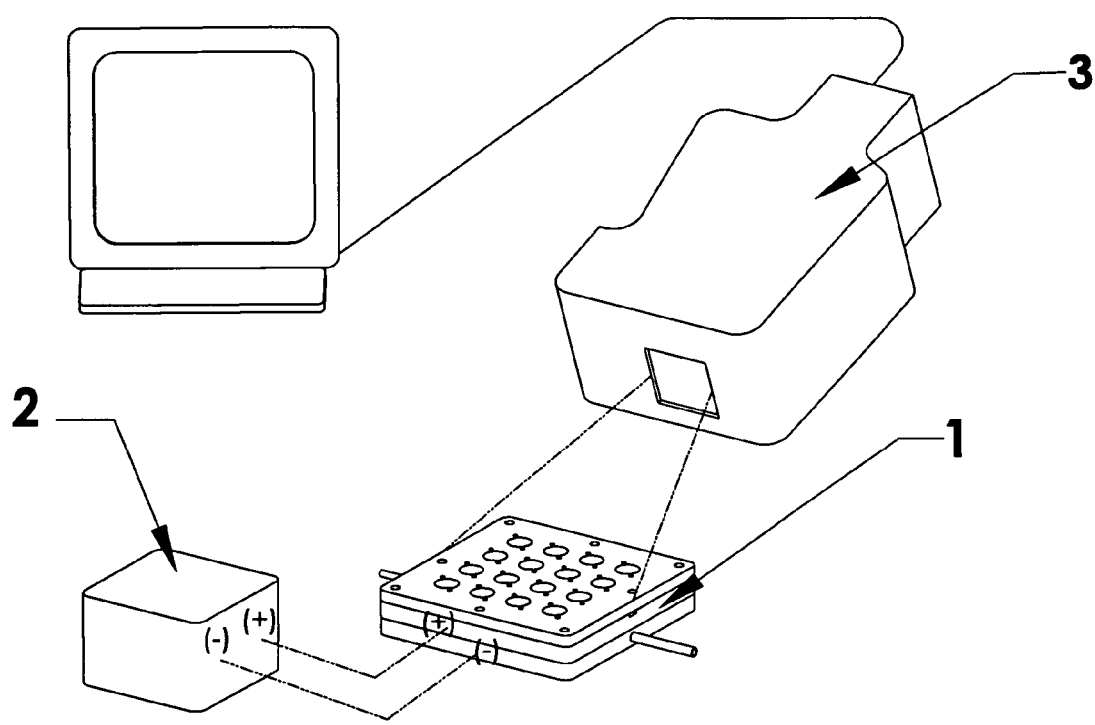
FIG. 1 is a schematic representation of a first embodiment of the combinatorial screening apparatus in accordance with the invention.

The present invention relates to the design of a new electrochemical combinatorial screening device and methods for discovering and evaluating electro-catalysts and other electrochemical materials. The device comprises a number of separate parts including an array of sample electrodes or electrode compositions in an electrochemical cell, a single electronic load for applying a voltage or current to the array, and an instrument for simultaneously monitoring the temperature of each electrode when the load is applied.

Rather than individually measuring the current passing through each sample electrode in response to an applied voltage, the device of the invention simultaneously monitors the equilibrium temperature at each sample electrode. The equilibrium temperature of the electrodes at any point in time during operation is dependent on the current passing through the electrode, $I_x$, and the electrode electrochemical resistance, $R_x$. The equilibrium temperature is also dependent on the rate of heat loss from the cell to the surrounding environment. Assuming equilibrium conditions have been reached, the relationship between the temperature at each electrode and the current passing through it under constant voltage conditions can be described by the equation: $\Delta T_x \propto P_x = I_x^2 R_x = I_x V_x = I_x V_T$, where $\Delta T_x$ is the temperature of an individual electrode, x; $P_x$ is the power associated with the individual electrode; $I_x$ is the current passing through the electrode; $R_x$ is the resistance of the electrode; and $V_x = V_T$ is the applied voltage. When a voltage is applied to the system, the temperature of the individual electrodes increases according to the relationship until the rate of heat generated at the cell is equal to the rate of heat loss from the cell. The resulting equilibrium temperature of the individual electrodes provides an indirect measurement of the relative efficiency of the materials comprising each electrode. The device of the invention can be used to screen a large array of electrochemical material compositions to identify the compositions that exhibit the greatest electrochemical efficiency.

In one mode of operation, the apparatus may be utilized by applying a single voltage to a cell comprising an array of electrodes of different compositions. When all of the electrodes are held at the same voltage, the greatest current passes through the electrodes with the lowest effective resistance and greatest electrochemical efficiency. In the device of the invention, these more efficient electrode compositions are identified, external to the cell, by their proportionally greater increase in temperature. If desired, the current passing through each sample electrode can be determined from the total cell voltage, the total current passing through the cell and the change in temperature relative to the other sample electrodes.

For the purpose of this invention an electrochemical cell comprises at least two electrode layers, e.g., a cathode and an anode, where a chemical entity is oxidized or reduced respectively. Either or both the anode and cathode may comprise an array of electrodes contained within the electrochemical cell. The electrochemical cell may also comprise a third, reference electrode. The electrochemical cell may also contain a membrane, which conducts ions but not electrons. The membrane may be a single-phase material such as the proton conductor, Nafion, or a multiphase material such as a porous polymer separator impregnated with a liquid electrolyte. An electrochemical material is any material that could be used in an electrochemical cell. Some examples of electrochemical materials include catalysts, active anode and cathode materials for battery, fuel cell and capacitor systems such as carbons, metals, alloys and metal oxides, membranes and separators, and electrolytes. Electrochemical processes that are of interest for screening include, electrocatalysis, intercalation, conversion reactions, double layer formation, and ion diffusion. The electronic load of the device is capable of both applying a constant voltage to the electrochemical cell and of monitoring the resulting current or of both applying a constant current to the electrochemical cell and of monitoring the resulting voltage. The temperature-monitoring instrument may be an IR camera or other thermal imaging device or an array of thermocouples or other device for measuring temperature.

FIG. 1 shows a simple schematic of one embodiment of the present invention. An electrochemical cell body 1 may contain an array of sample electrodes that are electrically connected to form a single working electrode. In this example, the working electrode is the positive cathode but it could also be the negative anode depending on the materials and electrochemical processes of interest. Each sample electrode in the array may comprise a different material composition to be screened for electrochemical performance. The electrodes in the array are essentially thermally isolated from each other but are all connected electrically to each other. The counter electrode, or in this example the negative anode, may comprise an array of electrodes of the same material composition or may comprise one or more common electrodes of the same material composition. The one or more electrodes comprising the counter electrode of the electrochemical cell body 1 are electrically connected to each other. The working electrode and counter electrode of the electrochemical cell body 1 may be connected to a single electronic load 2 that applies a constant current or voltage. An IR camera 3 or other device for measuring and recording temperature may be located adjacent to the electrochemical cell body 1 for simultaneous monitoring of the temperatures of the individual sample electrodes of the working electrode. The electronic load 2 may apply a constant voltage or current to the electrochemical cell body 1 and the individual electrodes may increase in temperature according to their inherent efficiency. The temperature change vs. time of the individual sample electrodes may be observed and recorded by the IR camera 3.

The invention has several advantages over current combinatorial screening methods used for electrochemical systems. Unlike other indirect screening methods for electrochemical systems, the temperature of the electrodes can be monitored external to the cell allowing for the use of conventional cell structures and designs within the cell body for more accurate evaluation of the materials of interest. The present invention may also be effectively scaled up to tens or hundreds of samples with little corresponding increase in cost and complexity because there is no need for additional leads and current monitoring channels. Thus the combinatorial screening apparatus and methods of this invention allow long term testing of new electrochemical materials to be performed more efficiently and accurately in conventional cell environments at much lower cost for equipment and labor.

Figure 2:
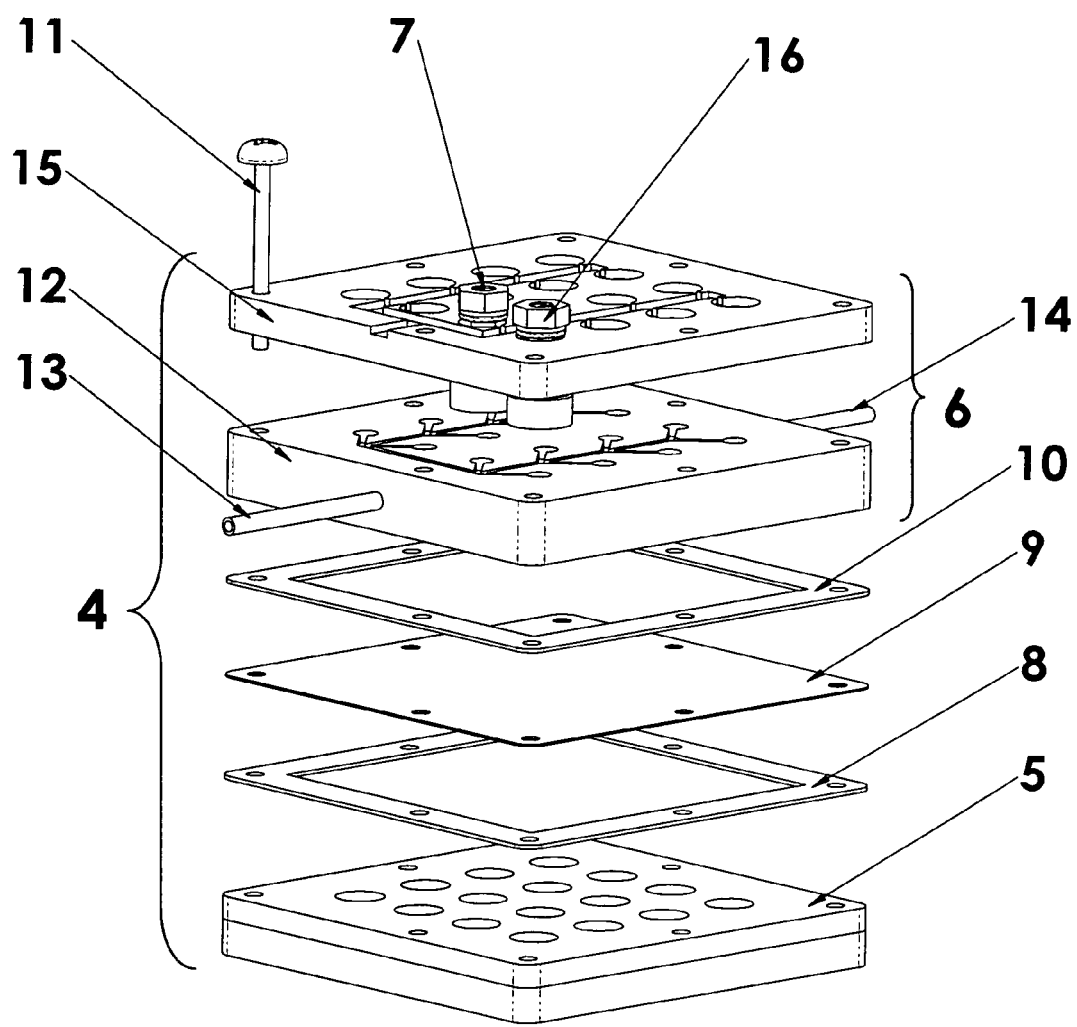
FIG. 2 is a schematic representation of a fuel cell assembly in accordance with the invention.

While not limited to a specific electrochemical reaction or material type, the device of the invention is particularly suited for screening electrochemical catalysts for fuel cells. A preferred embodiment of the invention comprises a fuel cell body with multiple sample electrodes. A schematic of the fuel cell body 4 of the present invention is shown in FIG. 2. The fuel cell body 4 may comprise a counter electrode block 5 and a working electrode block 6. In one embodiment, at least one of the fuel cell electrode blocks 5 and 6 may include openings to accommodate an array of sample electrodes 7. A gasket 8 may be disposed adjacent the counter electrode block 5. An ion conducting membrane 9, such as Nafion, or Nafion coated with a mixed phase carbon diffusion and electrolyte layer, or a membrane electrode assembly (MEA), may be disposed adjacent the gasket 8. For the purpose of the invention, the MEA includes the component of the fuel cell that contains the electrolyte system sandwiched between two catalytic layers. The electrolyte system may include a matrix that supports a liquid phase electrolyte or a polymer phase. The catalyst layers may comprise a carbon diffusion layer and electrolyte phase. The catalyst could be a powder dispersed within a mixed phase carbon diffusion and electrolyte layer or it may be in the form of a thin film applied to the sample electrode or to the membrane.

Adjacent the ion conducting membrane 9 may be disposed a second gasket 10. The electrode blocks 5 and 6 may be assembled facing each other to form a self-contained, closed fuel cell when all of the sample electrodes 7 are in place. The components of the fuel cell body are held together by bolts 11 that pass through the four corners of the cell electrode blocks. The gaskets 8 and 10 may provide an airtight seal between the counter electrode block 5 and the working electrode block 6 and the ion conducting membrane 9, which can withstand mild pressures of up to 20 psi.

An expanded view of the working electrode block 6 is also shown in FIG. 2. The working electrode block 6 may comprise two separate plates. A fuel flow plate 12 may provide channels for flowing fuel to the individual electrodes. The fuel flow plate 12 may also thermally isolate the individual electrodes 7 to prevent the behavior of any one electrode from affecting its neighbors. The fuel flow plate 12 can be made from a number of thermally insulating rigid materials such as acrylic or polyethylene. The fuel flow plate 12 may also be chemically stable to the fuel cell environment. The fuel flow plate 12 may include one fuel inlet 13 and one fuel outlet 14. In one embodiment the fuel flow plate 12 is capable of feeding fuel to each sample electrode 7 individually. Adjacent to the fuel flow plate 12 may be a rigid mounting plate 15. The mounting plate 15 may provide a rigid base for the attachment of the sample electrodes 7 and may be capable of maintaining even spacing and pressure across the face of the fuel cell. The mounting plate 15 can be made from a number of materials such as brass, stainless steel or Aluminum. In one embodiment, the sample electrodes 7 may be inserted from the bottom of the mounting plate 15 and fastened into place with a bolt 16. The sample electrodes 7 may provide both a thermal conduction and electrical conduction path to the outside of the fuel cell assembly.

Figure 3:
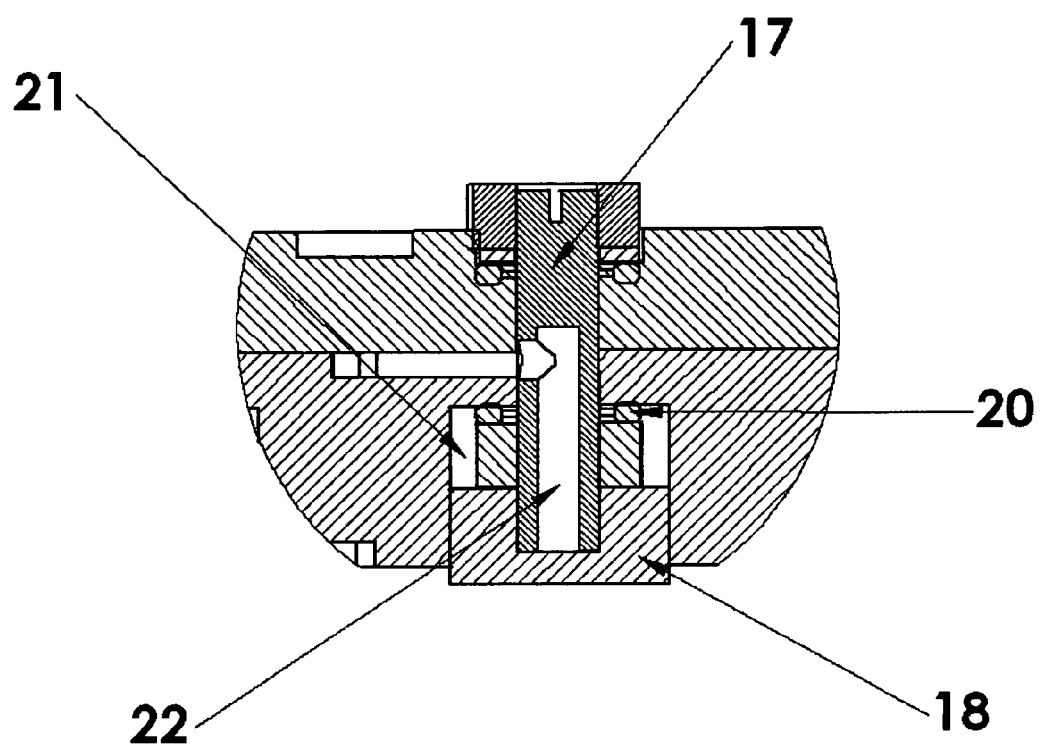
FIG. 3 is a cross-sectional view of a single electrode within the fuel cell assembly in accordance with the invention.

A cross-sectional view of a sample electrode mounted in an electrode block is shown in FIG. 3. The core of the sample electrode may include a thermally and electrically conductive rod 17 made of a non-porous material such as brass, copper or carbon. A thermally and electrically conductive electrode fuel diffusion layer 18 may be attached to the end of the conductive rod 17. In one embodiment the electrode fuel diffusion layer 18 may comprise a rigid, porous carbon disk. When the fuel cell is assembled, the catalyst or electrode material of interest for evaluation may be in physical and electrochemical contact with the face of the carbon diffusion layer 18.

At least one O-ring 19 may form a seal between the sample electrode and the fuel flow plate opening to separate the interior of the fuel cell from the exterior. In one embodiment, two O-rings 19 and 20 may form a sealed chamber 21 around the rod 17 within the dimensions of the electrode block. In this embodiment, a fuel flow path 22 perpendicular to the face of the diffusion layer may be provided from the chamber 21 through the conductive rod 17 and into the back of the fuel diffusion layer 18. Further in this embodiment the sides of the diffusion layer may be sealed with epoxy or other sealant such that the fuel flow path outlet from the sample electrode is only from the face of the carbon diffusion layer. A fuel flow outlet may be provided for each individual electrode. The fuel flow design of this embodiment provides fuel flow channels to each electrode individually.

In one aspect of the invention, the counter electrode plate has effectively the same design as the working electrode plate such that when assembled into a fuel cell the array of working and counter electrodes are paired together to form an electrochemical cell array with all of the cells connected in parallel. In another aspect, the counter electrode may comprise a single common electrode.

In another aspect of the invention, a method for screening electrochemical materials may include providing a plurality of electrochemical material compositions for screening followed by placing each material composition in an electrochemical cell associated with an individual sensor electrode. In one aspect of the invention, catalytic compositions for evaluation in the fuel cell apparatus of the invention may be prepared and evaluated in a number of ways. For example, a thin solid film of a catalytic layer may be deposited directly onto the electrode diffusion layer 18 using techniques such as electrochemical deposition or sputtering. When inserted into the fuel cell the catalytic layer may be pressed against the Nafion membrane or carbon diffusion electrolyte layer. Powdered forms of the catalyst compositions of interest may also be evaluated. For example, a powdered catalyst made by precipitation processes or high energy milling processes may be applied to carbon paper or directly to the membrane by making a slurry of the powdered catalyst with the electrolyte and a conductive additive. The slurry may be applied to the carbon paper or to the membrane 9 and the solvent removed by evaporation.

In one embodiment of the invention, when the catalyst layer is applied directly to the sample electrodes, such as by sputtering or by electro-deposition, the fuel cell may be assembled as follows. The sample electrodes 7 may be placed into their respective openings within the counter electrode block 5 and a working electrode block 6 and fastened into place with bolts 16. The counter electrode block 5 with all sample electrodes fastened in place may be placed on a flat surface. The gasket 8 may be placed on top of the counter electrode block 5. The membrane 9 or MEA may be placed on top of the gasket 8 followed by another gasket 10. The working electrode block 6 with the electrodes bolted in place may be placed on top of the stack. The fuel cell block may be fastened together with bolts 11 at each corner of the cell. If using the carbon paper method, the fuel cell may be assembled in a similar manner. However, the catalytic carbon paper disks may be either placed on top of the individual electrodes prior to applying the membrane, or the catalytic carbon disks may be placed onto the membrane in line with the sample electrodes prior to placing the electrode plate onto the membrane 9.

The next step in the method of the invention may include connecting the cells or electrodes electrically such that they can all be powered by a single load. For example, once the fuel cell block of the invention is assembled, the individual electrodes or cells may be connected electrically to provide a single positive lead from the cathode and a single negative lead from the anode. After the cells have been connected a single electrical load may be connected to the positive and negative leads of the cell body and used to apply a voltage or current to the cell array. For example, an electrical load could be used to apply a single voltage to the fuel cell body of the invention comprising an array of electrodes.

The last two steps in the method of the invention involve simultaneously monitoring the temperature increase of the sample electrodes after a load is applied and using the temperature change to determine the relative electrochemical efficiency of the material compositions being screened. For example, an IR camera adjacent to the fuel cell body of the invention may be used to simultaneously monitor the temperature increase of the individual sample electrodes in the electrode array. The relative temperature increases of the sample electrodes may be used as a measure of the relative efficiency of the catalyst compositions comprising the individual electrodes assuming that all other factors contributing to the observed temperature increase are the same or that they have been minimized for each cell. The ratio of the temperature increases between the separate sample electrodes may be used to determine the current passing through each electrode if the total voltage and current of the fuel cell body is known. The best materials may be identified and used as controls in subsequent screening arrays. The best materials may also be removed from the device for compositional analysis of the catalyst sample.

The method of the invention may be readily adapted to other electrochemical processes such as the evaluation of battery or ultracapacitor materials and components. For example, a number of Li-ion battery cathode materials may be synthesized by firing different ratios of starting materials in a furnace to provide a range of material compositions. Electrodes containing the material compositions may be prepared by conventional coating techniques. Individual electrodes for evaluation may be punched out or cut from the coated electrode for insertion into an electrochemical cell array for evaluation as previously described.

It must be emphasized that the example below is merely illustrative of specific embodiments of the invention and is not intended as an undue limitation on the generally broad scope of the invention.

EXAMPLE 1

Catalyst compositions were prepared by electrodeposition directly onto the carbon disk fuel diffusion layer 18. A PAR potentiostat with a Hokuto Denko controller was used to polarize the electrodes to a specific potential for times ranging from a few seconds to several minutes. The deposition solution consisted of 20 mM solutions of $H_2PtCL_6 \cdot 6H_2O$, $NiSO_4$, and $CoSO_4$ and mixtures of these solutions (pH~3) for the deposition of the Pt alloys. A large, carbon disk counter electrode faced the working electrode with a stir bar in between the two electrodes. A SCE electrode was used as a reference. From scanning electron microscopy images, the Pt alloy films deposited onto the electrodes were porous due to the porous nature of the carbon substrate. The counter electrodes contained high surface area Pt powder carbon to minimize any contribution to the cell resistance and to ensure any difference in signal was due to the working electrodes.

Figure 4:
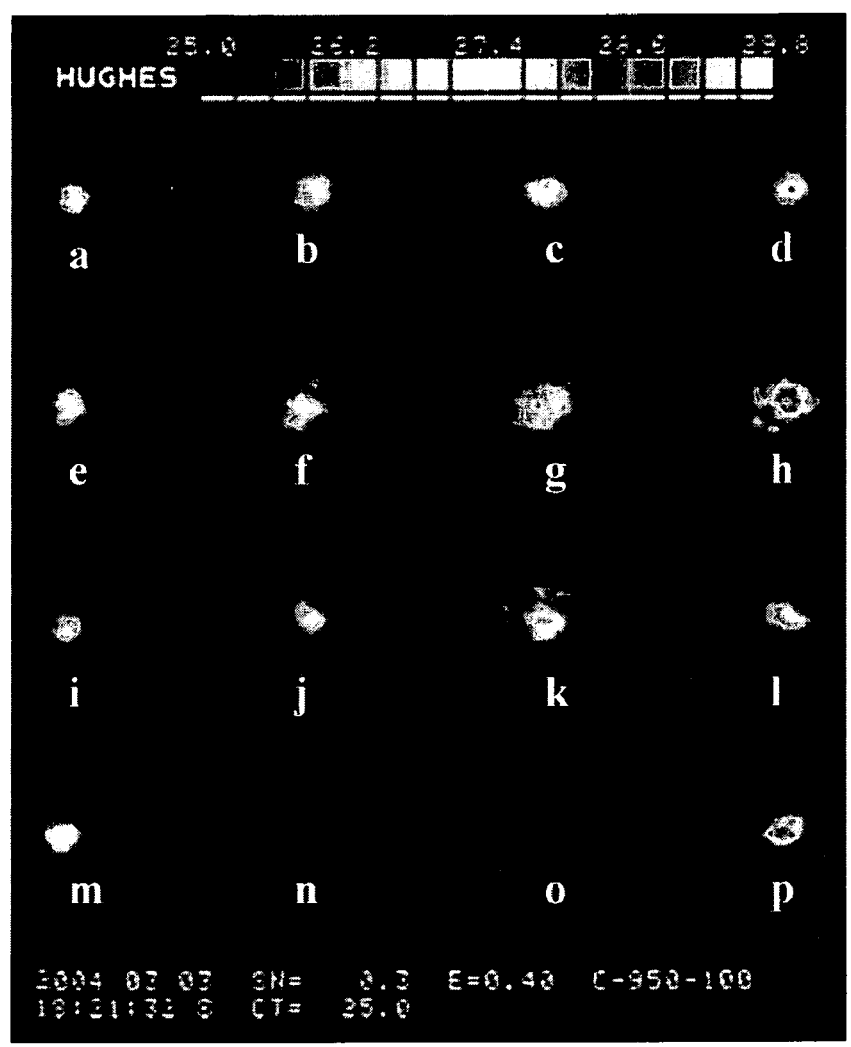
FIG. 4 is an infrared image obtained by the first embodiment in accordance with the invention.

The electrodes were inserted into their respective openings and fastened with nuts. The fuel cell was assembled and fastened together. The fuel cell assembly was connected to a single load with the positive lead connected to the working electrode plate and the negative lead connected to the counter electrode plate. A hydrogen gas line was connected to the inlet for the counter electrode and an oxygen gas line was connected to the inlet for the working electrode. FIG. 4 shows an IR camera image (Hughes) taken of the fuel cell in operation. The fuel cell conditions were $H_2$: flow rate: 100 mL/min; Pressure: 20 Psi, $O_2$ flow rate: 75 ML/min.; pressure: 20 Psi, Steamer temp: 90° C., 2A load, and Cell Voltage ~0.75 V. The image was taken after conditioning and almost a full day of operation. The sample electrodes labeled n and o had no catalyst applied to the carbon disk fuel diffusion layer, and were used as controls. The electrodes with no catalyst exhibited very little temperature increase indicating that they had a high effective resistance related to the poor efficiency of carbon as a catalyst for oxygen reduction. The greatest sample electrode temperature increase was observed for sample electrodes h, k and p, on which pure Pt was electrodeposited. The greater temperature indicates that the sample electrodes coated with pure Pt catalysts had a low effective resistance due to the high efficiency of the Pt catalyst. The other electrodes in the array were coated with various alloys of Pt and as a group showed a temperature changes somewhere between carbon and Pt. The relative temperature changes of the electrodes in the sample array indicate that pure platinum metal has the best efficiency of the catalyst compositions evaluated.

The foregoing description of the embodiments of the invention has been presented for the purposes of illustration and description. It is not intended to be exhaustive or to limit the invention to the precise form disclosed. Many modifications and variations are possible in light of the above teaching.

It is intended that the scope of the invention be limited not by this detailed description, but rather by the claims appended hereto.

We claim:

1. A combinatorial screening apparatus for electrochemical materials comprising:
    an array of electrochemical cells (1); and
    a device (3) operable to simultaneously monitor temperature changes at each electrochemical cell arising from application of a potential across the array of electrochemical cells.

2. The apparatus of claim 1, wherein the electrochemical cells (1) are connected in parallel.

3. The apparatus of claim 1, wherein the device (3) comprises a thermal imaging device.

4. The apparatus of claim 1, wherein the array of electrochemical cells (1) share at least one common membrane.

5. The apparatus of claim 1, wherein the array of electrochemical cells (1) share at least one common electrode.

6. The apparatus of claim 1, further comprising a catalyst.

7. The apparatus of claim 1, wherein the array of electrochemical cells (1) are configured to operate in a fuel cell.

8. The apparatus of claim 7, further comprising a fuel flow block (12) wherein each electrochemical cell has an isolated fuel inlet (13).

9. The apparatus of claim 8, wherein each electrochemical cell has an isolated gas diffusion layer (18).

10. The apparatus of claim 9, wherein each isolated fuel inlet (13) is disposed substantially perpendicular to a corresponding isolated gas diffusion layer (18).

11. The apparatus of claim 10, wherein each electrochemical cell has an isolated fuel outlet (14).

12. An apparatus for the evaluation of electrochemical materials using a single voltage source comprising:
    an array of electrochemical cells; and
    a thermal imaging device operable to simultaneously monitor temperature changes at each electrochemical cell arising from application of a voltage across the array of electrochemical cells.

13. The apparatus of claim 12, wherein the electrochemical cells are connected in parallel.

14. A combinatorial screening apparatus for electrochemical materials comprising:
    an array of electrochemical cells;
    a source of a voltage potential in electrical communication with each electrochemical cell of said array; and
    a device in thermal communication with said array to concurrently detect thermal wavelengths propagating away from each electrochemical cell of the array.

15. The apparatus as recited in claim 14, wherein the electrochemical cells are connected in parallel.

16. The apparatus as recited in claim 14 wherein the array of electrochemical cells share a common membrane.

17. The apparatus as recited in claim 14 wherein the array of electrochemical cells share a common electrode.

18. The apparatus as recited in claims 14 further comprising a catalyst.

19. The apparatus as recited in claim 18 further comprising a fuel flow block, with each electrochemical cell further including an isolated fuel inlet and an isolated gas diffusion layer.

20. The apparatus as recited in claim 19 wherein the isolated fuel inlet is disposed substantially perpendicular to the isolated gas diffusion layer and each electrochemical cell further including an isolated fuel outlet.

* * * * *